United States Patent
Kim et al.

(10) Patent No.: US 10,544,427 B2
(45) Date of Patent: Jan. 28, 2020

(54) TRANSGENIC MOUSE MODEL FOR DEMENTIA

(71) Applicant: Korea Institute of Science and Technology, Seoul (KR)

(72) Inventors: Do Hee Kim, Seoul (KR); Seul Gi Shin, Seoul (KR); Sung Su Lim, Seoul (KR); Ae Nim Pae, Seoul (KR); Dong Jin Kim, Seoul (KR); Yun Kyung Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/709,822

(22) Filed: Sep. 20, 2017

(65) Prior Publication Data
US 2018/0119169 A1 May 3, 2018

(30) Foreign Application Priority Data

Oct. 10, 2016 (KR) ........................ 10-2016-0130813

(51) Int. Cl.
| A01K 67/027 | (2006.01) |
| C12N 15/85 | (2006.01) |
| C07K 14/47 | (2006.01) |
| G01N 33/50 | (2006.01) |
| G01N 33/68 | (2006.01) |

(52) U.S. Cl.
CPC ...... *C12N 15/8509* (2013.01); *A01K 67/0275* (2013.01); *C07K 14/47* (2013.01); *G01N 33/5058* (2013.01); *G01N 33/5088* (2013.01); *G01N 33/6896* (2013.01); *A01K 2207/15* (2013.01); *A01K 2217/05* (2013.01); *A01K 2217/206* (2013.01); *A01K 2227/105* (2013.01); *A01K 2267/0312* (2013.01); *A01K 2267/0318* (2013.01); *C07K 2319/60* (2013.01); *C12N 2015/859* (2013.01); *C12N 2015/8527* (2013.01); *C12N 2015/8536* (2013.01); *C12N 2830/008* (2013.01); *G01N 2800/2814* (2013.01)

(58) Field of Classification Search
CPC . A01K 67/0275; C07K 14/47; C12N 15/8509
See application file for complete search history.

(56) References Cited

U.S. PATENT DOCUMENTS

| 8,778,343 | B2 | 7/2014 | Kayed | |
| 2002/0018995 | A1* | 2/2002 | Ghetti | ................ A61K 38/1709 435/6.16 |

| 2013/0209453 | A1 | 8/2013 | Black et al. |
| 2014/0011197 | A1 | 1/2014 | Goldstein et al. |
| 2014/0161875 | A1 | 6/2014 | Winderickx et al. |

OTHER PUBLICATIONS

Tak et al , PLOSOne, 12, 287682 (Year: 2013).*
Zilca et al, FEBS Letters 580, 3582-3588 (Year: 2006).*
Andra et al Neurobiology of Aging, 17: 183-190 (Year: 1996).*
Gama Sosa et al Brain Struct Funct 214:91-109 (Year: 2010).*
Sigmund Arterioscler Thromb Vase Biol, 1425-1429 (Year: 2000).*
Chesselet and Carmichael Neurotherapeutics 9:241-244 (Year: 2012).*
Bailey et al Alzheimer's and Dementia, 7(4)S515-S516 (Year: 2011).*
Moy et al Behavioral Brain Research 191, 118-129 (Year: 2008).*
Kim et al Neurodegenerative Diseases, vol. 17, Supp. Supplement 1, pp. 1140. Abstract Number: p. 1 (Year: 2017).*
Lim et al Computational and Structural Biotechnology Journal 12, 7-13 (Year: 2014).*
Kim et al Neurodegenerative Diseases, vol. 17, Supplement 1, pp. 1140 (Year: 2017).*
Kim et al Molecular Imaging and Biology, vol. 18, No. 2, Supp. Supplement, pp. s560 (Year: 2016).*
Tania F. Gendron et al., "The role of tau in neurodegeneration", Molecular Neurodegeneration, Mar. 2009, pp. 1-19, vol. 4, No. 13.
Roland Brandt et al., "Tau alteration and neuronal degeneration in tauopathies: mechanisms and models", Biochimica et Biophysica Acta, 2005, pp. 331-354, vol. 1739.
Tom K. Kerppola, "Bimolecular Fluorescence Complementation (BiFC) Analysis as a Probe of Protein Interactions in Living Cells", Annu. Rev. Biophys., 2008, pp. 465-487. vol. 37.

(Continued)

*Primary Examiner* — Anoop K Singh
(74) *Attorney, Agent, or Firm* — Rabin & Berdo, P.C.

(57) ABSTRACT

Disclosed is a vector pair for screening tau oligomer formation, a mouse embryo introduced with the vector pair, a transgenic model mouse of neurological disease, obtained from the mouse embryo, and a method of screening a tau oligomer formation inhibitor candidate using the transgenic model mouse. More specifically, the present invention provides vector pair for screening tau oligomer formation, comprising: a first vector comprising a first tau gene, a first fluorescence protein gene and a first neuron-specific promoter; and a second vector comprising a second tau gene, a second fluorescence protein gene and a second neuron-specific promoter, wherein a protein expressed from the first fluorescence protein gene and a protein expressed from the second fluorescence protein gene bind to each other to display fluorescence, by association between a protein expressed from the first tau gene and a protein expressed from the second tau gene.

2 Claims, 11 Drawing Sheets

Specification includes a Sequence Listing.

(56) References Cited

OTHER PUBLICATIONS

Y. John Shyu et al., "Identification of new fluorescent protein fragments for bimolecular fluorescence complementation analysis under physiological conditions", BioTechniques, Jan. 2006, pp. 61-66, vol. 40.

Yutaka Kodama et al., "An improved bimolecular fluorescence complementation assay with a high signal-to-noise ratio", BioTechniques, Nov. 2010, pp. 793-805, vol. 49.

* cited by examiner

SEQUENCE LISTING

```
<160> NUMBER OF SEQ ID NOS: 9

<210> SEQ ID NO 1
<211> LENGTH: 1323
<212> TYPE: DNA
<213> ORGANISM: Homo sapiens

<400> SEQUENCE: 1
atggctgagc cccgccagga gttcgaagtg atggaagatc acgctgggac gtacgggttg        60
```

| | |
|---|---|
| ggggacagga aagatcaggg gggctacacc atgcaccaag accaagaggg tgacacggac | 120 |
| gctggcctga aagaatctcc cctgcagacc cccactgagg acggatctga ggaaccgggc | 180 |
| tctgaaacct ctgatgctaa gagcactcca acagcggaag atgtgacagc acccttagtg | 240 |
| gatgagggag ctcccggcaa gcaggctgcc gcgcagcccc acgcgagat cccagaagga | 300 |
| accacagctg aagaagcagg cattggagac accccagcc tggaagacga agctgctggt | 360 |
| cacgtgaccc aagctcgcat ggtcagtaaa agcaaagacg ggactggaag cgatgacaaa | 420 |
| aaagccaagg gggctgatgg taaaacgaag atcgccacac cgcggggagc agcccctcca | 480 |
| ggccagaagg gccaggccaa cgccaccagg attccagcaa aaaccccgcc cgctccaaag | 540 |
| acaccaccca gctctggtga acctccaaaa tcaggggatc gcagcggcta cagcagcccc | 600 |
| ggctccccag cactcccgg cagccgctcc cgcaccccgt cccttccaac cccacccacc | 660 |
| cgggagccca agaaggtggc agtggtccgt actccaccca gtcgccgtc ttccgccaag | 720 |
| agccgcctgc agacagcccc cgtgcccatg ccagacctga gaatgtcaa gtccaagatc | 780 |
| ggctccactg agaacctgaa gcaccagccg ggaggcggga aggtgcagat aattaataag | 840 |
| aagctggatc ttagcaacgt ccagtccaag tgtggctcaa aggataatat caaacacgtc | 900 |
| ctgggaggcg gcagtgtgca aatagtctac aaaccagttg acctgagcaa ggtgacctcc | 960 |
| aagtgtggct cattaggcaa catccatcat aaaccaggag gtggccaggt ggaagtaaaa | 1020 |
| tctgagaagc ttgacttcaa ggacagagtc cagtcgaaga ttgggtccct ggacaatatc | 1080 |
| acccacgtcc ctggcggagg aaataaaaag attgaaaccc acaagctgac cttccgcgag | 1140 |
| aacgccaaag ccaagacaga ccacggggcg gagatcgtgt acaagtcgcc agtggtgtct | 1200 |
| ggggacacgt ctccacggca tctcagcaat gtctcctcca ccggcagcat cgacatggta | 1260 |
| gactcgcccc agctcgccac gctagctgac gaggtgtctg cctccctggc caagcagggt | 1320 |
| ttg | 1323 |

<210> SEQ ID NO 2
<211> LENGTH: 42
<212> TYPE: DNA
<213> ORGANISM: Artificial Sequence
<220> FEATURE:
<223> OTHER INFORMATION: VN173 linker

<400> SEQUENCE: 2

| | |
|---|---|
| acgcgtacgc ggccgctcga gtctagaaga tccatcgcca cc | 42 |

<210> SEQ ID NO 3
<211> LENGTH: 522
<212> TYPE: DNA
<213> ORGANISM: Artificial Sequence
<220> FEATURE:
<223> OTHER INFORMATION: VN173

<400> SEQUENCE: 3

| | |
|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagct gatctgcacc accggcaagc tgcccgtgcc ctggcccacc | 180 |
| ctcgtgacca cctgggcta cggcctgcag tgcttcgccc gctacccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |

```
aagctggagt acaactacaa cagccacaac gtctatatca ccgccgacaa gcagaagaac    480
ggcatcaagg ccaacttcaa gatccgccac aacatcgagt ag                       522
```

<210> SEQ ID NO 4
<211> LENGTH: 24
<212> TYPE: DNA
<213> ORGANISM: Artificial Sequence
<220> FEATURE:
<223> OTHER INFORMATION: VC155 linker

<400> SEQUENCE: 4

```
acgcgtacgc ggccgctcga gaag                                            24
```

<210> SEQ ID NO 5
<211> LENGTH: 249
<212> TYPE: DNA
<213> ORGANISM: Artificial Sequence
<220> FEATURE:
<223> OTHER INFORMATION: VC155

<400> SEQUENCE: 5

```
cagaagaacg gcatcaaggc caacttcaag atccgccaca acatcgagga cggcggcgtg    60
cagctcgccg accactacca gcagaacacc cccatcggcg acggccccgt gctgctgccc   120
gacaaccact acctgagcta ccagtccaaa ctgagcaaag accccaacga gaagcgcgat   180
cacatggtcc tgctggagtt cgtgaccgcc gccgggatca ctctcggcat ggacgagctg   240
tacaagtaa                                                            249
```

<210> SEQ ID NO 6
<211> LENGTH: 2816
<212> TYPE: DNA
<213> ORGANISM: Artificial Sequence
<220> FEATURE:
<223> OTHER INFORMATION: pTSC21K-TauP301L-VN173

<400> SEQUENCE: 6

```
gagctctata ggtcttaagt tccagaagaa acgtaatgaa gtcacccagc aggaggtgct    60
cagggacagc aagacacaca cacccaggac actaggctcc cacttccttg gctttctctg   120
agtggcaaag gaccttaggc agtgtcactc cctaagagaa ggggataaag agaggggctg   180
aggtattcag tcatgtgctc cgtggatctc aagccctcaa ggtaaatggg acccacctg    240 tcctaccagc tggctgacct gtagctttcc ccaccacaga atccaagtcg gaactcttgg   300
cacctagagg atctcgactg gatccggtac cgaggagatc tgccgccgcg atcgccatgg   360
ctgagccccg ccaggagttc gaagtgatgg aagatcacgc tgggacgtac gggttggggg   420
acaggaaaga tcagggggc tacaccatgc accaagacca agagggtgac acggacgctg   480
gcctgaaaga atctccccctg cagacccca ctgaggacgg atctgaggaa ccgggctctg   540
aaacctctga tgctaagagc actccaacag cggaagatgt gacagcaccc ttagtggatg   600
agggagctcc cggcaagcag gctgccgcgc agccccacac ggagatccca aaggaacca   660 cagctgaaga agcaggcatt ggagacaccc cagcctgga agacgaagct gctggtcacg   720
tgacccaagc tcgcatggtc agtaaaagca agacggac tggaagcgat gacaaaaaag   780 ccaaggggc tgatggtaaa acgaagatcg ccacaccgcg gggagcagcc cctccaggcc   840
agaagggcca ggccaacgcc accaggattc agcaaaaac cccgcccgct ccaaagacac   900
cacccagctc tggtgaacct ccaaaatcag gggatcgcag cggctacagc agccccggct   960
```

| | |
|---|---:|
| ccccaggcac tcccggcagc cgctcccgca ccccgtccct tccaaccccca cccacccggg | 1020 |
| agcccaagaa ggtggcagtg gtccgtactc cacccaagtc gccgtcttcc gccaagagcc | 1080 |
| gcctgcagac agcccccgtg cccatgccag acctgaagaa tgtcaagtcc aagatcggct | 1140 |
| ccactgagaa cctgaagcac cagccgggag gcgggaaggt gcagataatt aataagaagc | 1200 |
| tggatcttag caacgtccag tccaagtgtg gctcaaagga taatatcaaa cacgtcctgg | 1260 |
| gaggcggcag tgtgcaaata gtctacaaac cagttgacct gagcaaggtg acctccaagt | 1320 |
| gtggctcatt aggcaacatc catcataaac caggaggtgg ccaggtggaa gtaaaatctg | 1380 |
| agaagcttga cttcaaggac agagtccagt cgaagattgg gtccctggac aatatcaccc | 1440 |
| acgtccctgg cggaggaaat aaaaagattg aaacccacaa gctgaccttc cgcgagaacg | 1500 |
| ccaaagccaa gacagaccac ggggcggaga tcgtgtacaa gtcgccagtg gtgtctgggg | 1560 |
| acacgtctcc acggcatctc agcaatgtct cctccaccgg cagcatcgac atggtagact | 1620 |
| cgccccagct cgccacgcta gctgacgagg tgtctgcctc cctggccaag cagggttttga | 1680 |
| cgcgtacgcg gccgctcgag tctagaagat ccatcgccac catggtgagc aagggcgagg | 1740 |
| agctgttcac cggggtggtg cccatcctgg tcgagctgga cggcgacgta aacggccaca | 1800 |
| agttcagcgt gtccggcgag ggcgagggcg atgccaccta cggcaagctg accctgaagc | 1860 |
| tgatctgcac caccggcaag ctgcccgtgc cctggcccac cctcgtgacc accctgggct | 1920 |
| acggcctgca gtgcttcgcc cgctaccccg accacatgaa gcagcacgac ttcttcaagt | 1980 |
| ccgccatgcc cgaaggctac gtccaggagc gcaccatctt cttcaaggac gacggcaact | 2040 |
| acaagacccg cgccgaggtg aagttcgagg gcgacaccct ggtgaaccgc atcgagctga | 2100 |
| agggcatcga cttcaaggag gacggcaaca tcctggggca caagctggag tacaactaca | 2160 |
| acagccacaa cgtctatatc accgccgaca gcagaagaa cggcatcaag gccaacttca | 2220 |
| agatccgcca caacatcgag tagggatccc gggtggcatc cctgtgaccc ctccccagtg | 2280 |
| cctctcctgg ccctggaagt ttaaacggcc ggccgcggtc atagctgttt cctgaacaga | 2340 |
| tcccgggtgg catccctgtc gaggtccttc ctctgcagag gtcttgcttc tcccggtcag | 2400 |
| ctgactccct ccccaagtcc ttcaaatatc tcagaacatg gggagaaacg gggaccttgt | 2460 |
| ccctcctaag gaaccccagt gctgcatgcc atcatccccc ccaccctcgc ccccaccccc | 2520 |
| gccacttctc cctccatgca taccactagc tgtcattttg tactctgtat ttattctagg | 2580 |
| gctgcttctg attatttagt ttgttctttc cctggagacc tgttagaaca taagggcgta | 2640 |
| tggtgggtag gggaggcagg atatcagtcc cctggggcga gttcctccct gccaaccaag | 2700 |
| ccagatgcct gaaagagata tggatgaggg aagttggact gtgcctgtac ctggtacagt | 2760 |
| catactctgt tgaaagaatc atcggggagg ggggggggct caagagggga gagctc | 2816 |

<210> SEQ ID NO 7
<211> LENGTH: 2510
<212> TYPE: DNA
<213> ORGANISM: Artificial Sequence
<220> FEATURE:
<223> OTHER INFORMATION: pTSC21K-TauP301L-VC155

<400> SEQUENCE: 7

| | |
|---|---:|
| gagctctata ggtcttaagt tccagaagaa acgtaatgaa gtcacccagc aggaggtgct | 60 |
| cagggacagc aagacacaca cacccaggac actaggctcc cacttccttg gctttctctg | 120 |
| agtggcaaag gaccttaggc agtgtcactc cctaagagaa ggggataaag agaggggctg | 180 |
| aggtattcag tcatgtgctc cgtggatctc aagccctcaa ggtaaatggg gacccacctg | 240 |

```
tcctaccagc tggctgacct gtagctttcc ccaccacaga atccaagtcg gaactcttgg    300
cacctagagg atctcgactg gatccggtac cgaggagatc tgccgccgcg atcgccatgg    360
ctgagccccg ccaggagttc gaagtgatgg aagatcacgc tgggacgtac gggttggggg    420
acaggaaaga tcagggggc tacaccatgc accaagacca agagggtgac acggacgctg     480
gcctgaaaga atctcccctg cagaccccca ctgaggacgg atctgaggaa ccgggctctg    540
aaacctctga tgctaagagc actccaacag cggaagatgt gacagcaccc ttagtggatg    600
agggagctcc cggcaagcag gctgccgcgc agccccacac ggagatccca aaggaaccca    660
cagctgaaga agcaggcatt ggagacaccc ccagcctgga agacgaagct gctggtcacg    720
tgacccaagc tcgcatggtc agtaaaagca agacgggac tggaagcgat gacaaaaaag     780 ccaaggggc tgatggtaaa cgaagatcg ccacaccgcg gggagcagcc cctccaggcc      840
agaagggcca ggccaacgcc accaggattc cagcaaaaac cccgcccgct ccaaagacac    900
cacccagctc tggtgaacct ccaaaatcag gggatcgcag cggctacagc agccccggct    960
ccccaggcac tcccggcagc cgctcccgca ccccgtccct tccaaccccc cccacccggg   1020
agcccaagaa ggtggcagtg gtccgtactc caccccaagtc gccgtcttcc gccaagagcc  1080
gcctgcagac agccccgtg cccatgccag acctgaagaa tgtcaagtcc aagatcggct    1140
ccactgagaa cctgaagcac cagccggag gcgggaaggt gcagataatt aataagaagc    1200
tggatcttag caacgtccag tccaagtgtg gctcaaagga taatatcaaa cacgtcccgg   1260
gaggcggcag tgtgcaaata gtctacaaac cagttgacct gagcaaggtg acctccaagt   1320
gtggctcatt aggcaacatc catcataaac caggaggtgg ccaggtggaa gtaaaatctg   1380
agaagcttga cttcaaggac agagtccagt cgaagattgg gtccctggac aatatcaccc   1440
acgtccctgg cggaggaaat aaaaagattg aaacccacaa gctgaccttc cgcgagaacg   1500
ccaaagccaa gacagaccac ggggcggaga tcgtgtacaa gtcgccagtg gtgtctgggg   1560
acacgtctcc acggcatctc agcaatgtct cctccaccgg cagcatcgac atggtagact   1620
cgccccagct cgccacgcta gctgacgagg tgtctgcctc cctggccaag cagggtttga   1680
cgcgtacgcg gccgctcgag aagcagaaga acggcatcaa ggccaacttc aagatccgcc   1740
acaacatcga ggacggcggc gtgcagctcg ccgaccacta ccagcagaac cccccatcg    1800 gcgacggccc cgtgctgctg cccgacaacc actacctgag ctaccagtcc aaactgagca   1860
aagaccccaa cgagaagcgc gatcacatgg tcctgctgga gttcgtgacc gccgccggga   1920
tcactctcgg catggacgag ctgtacaagt aagcggccgc ggggatccag acatgataag   1980
atacattgat gagtttaaac ggccggccgc ggtcatagct gtttcctgaa cagatcccgg   2040
gtggcatccc tgtcgaggtc cttcctctgc agaggtcttg cttctcccgg tcagctgact   2100
ccctccccaa gtccttcaaa tatctcagaa catggggaga acgggggacc ttgtccctcc   2160
taaggaaccc cagtgctgca tgccatcatc ccccccaccc tcgccccac cccgccact     2220 tctccctcca tgcataccac tagctgtcat tttgtactct gtatttattc tagggctgct   2280
tctgattatt tagtttgttc tttcccttgga gacctgttag aacataaggg cgtatggtgg   2340
gtaggggagg caggatatca gtcccctggg gcgagttcct ccctgccaac caagccagat   2400
gcctgaaaga gatatggatg agggaagttg gactgtgcct gtacctggta cagtcatact   2460
ctgttgaaag aatcatcggg gaggggggg ggctcaagag gggagagctc              2510
```

<210> SEQ ID NO 8

```
<211> LENGTH: 31
<212> TYPE: DNA
<213> ORGANISM: Artificial Sequence
<220> FEATURE:
<223> OTHER INFORMATION: Forward primer (P301L-F)

<400> SEQUENCE: 8
aatatcaaac acgtcctggg aggcggcagt g                              31

<210> SEQ ID NO 9
<211> LENGTH: 27
<212> TYPE: DNA
<213> ORGANISM: Artificial Sequence
<220> FEATURE:
<223> OTHER INFORMATION: Reverse primer (P301L-R)

<400> SEQUENCE: 9
cacactgccg cctcccagga cgtgttt                                   27
```

TRANSGENIC MOUSE MODEL FOR DEMENTIA

BACKGROUND OF THE INVENTION

Field of the Invention

The present invention relates to a vector pair for screening tau oligomer formation, a mouse embryo introduced with the vector pair, a transgenic model mouse of neurological disease obtained from the mouse embryo, and a method of screening a tau oligomer formation inhibitor candidate using the transgenic model mouse.

Description of the Prior Art

Tau protein is a kind of microtubule-associated protein having a molecular weight of 50,000 to 70,000, which shows remarkable molecular diversity by its phosphorylation. In the human brain, six tau isoforms are generated by insertion of 29 or 58 amino acid residues in the N-terminal region and mRNA alternative splicing of 3 or 4 repeating structures (also referred to as microtubule-associated sites). It was previously thought that tau protein is specific for the central nervous system and found primarily in axons, but it is currently known that tau protein is expressed in astrocytes and oligodendroglia in relatively many tissues, as well as neurons, and is also found in dendrities in addition to axons. Tau contributes to the stability of microtubules, and the excessive aggregation of tau protein by phosphorylation causes various brain neurological diseases. Namely, central nervous diseases, including Alzheimer disease, fontotemporal lobar degeneration (FTLD), Pick's disease, corticobasal degeneration (CBD), progressive supranuclear palsy (PSP) and the like, are known to involve tau protein aggregates. Because of such pathological features, such neurological diseases are collectively called tauopathies. Tau protein aggregates appearing in tauopathy patients are mainly found in neuronal cell bodies and dendrite, called neurofibrillary tangles (NFT) and neuropil threads. Neurofibrillary tangles are composed of paired helical filaments (PHFs) of aggregated and hyperphosphorylated tau protein, unlike normal tau protein. Although the role of abnormal tau protein aggregation, which appears in tauopathies, in a severe disease stage, has not been clearly known, it is similar to an aggregation phenomenon that appears commonly in neurodegenerative brain diseases, including Huntington's disease, Parkinson's disease, Creutzfeldt-Jakob disease, and the like, and there is a significant correlation between neurofibrillary tangle formation and cognitive impairment. In this respect, it is evident that tau protein plays an important role.

A series of recent studies indicate that various tau oligomers rather than neurofibrillary tangles directly cause neuronal cell toxicity and are also metastasized to other sites of the brain to spread tauopathy. For example, Mirbaha et al. suggested tau trimers as structurally modified bases for intracellular tau, which can be received by cells. On the contrary, Michel et al. suggested that tau monomers are suitable fundamental metastatic forms, based on high-resolution imaging. In 2013, Wu et al. suggested that dimeric or trimeric tau having low molecular weight is a fundamental form that is metastasized between cells. Some studies on the isolation of tau protein and the identification of toxic tau oligomers by a series of biochemical experimental techniques were reported. However, direct observation of tau oligomers in the brain has not yet been reported, and the biggest reason why observation of tau oligomers is difficult is because of the absence of an experimental method that can specifically distinguish tau oligomers in the early stage of aggregation from normal tau protein present in large amounts. Regarding methods for detecting tau aggregates in neurons, immunotherapeutic technology using tau antibodies (U.S. Pat. No. 8,778,343, and US Patent Publication Nos. 2013-0209453 and 2014-0161875), and a tau-related disease cell model based on stem cells (US Patent Publication No. 2014-0011197) were developed. However, the development of technology related to cell models enabling real-time monitoring of tau aggregation mechanisms in living cells is still insufficient.

SUMMARY OF THE INVENTION

The present inventors have developed a method for constructing a transgenic model mouse of neurological disease, which displays fluorescence in the brain upon tau oligomer formation. The developed transgenic model mouse is a transgenic model mouse in which tau oligomer formation can be detected by a bimolecular fluorescence complementation (BiFC) technique. Particularly, the present invention provides a transgenic mouse in which tau oligomer formation in living tissue can be detected. Thus, the present invention makes it possible to directly detect tau oligomer formation in tissue, particularly the brain, and to screen a tau oligomer formation inhibitor. Furthermore, the present invention makes it possible to screen a tau oligomer formation inhibitor candidate and access an agent for treating neurological disease such as dementia whose perfect curing method has not yet been developed.

Objects to be solved by the present invention are not limited to the above-mentioned objects, and other objects that are not mentioned herein may be clearly understood by those skilled in the art from the following description.

Hereinafter, various embodiments of the present invention will be described with reference to the accompanying drawings.

The present invention can be embodied in a variety of different forms and may have various embodiments, and exemplary embodiments are illustrated in the accompanying drawings and will be described in detail in the detailed description. However, it should be understood that the present invention is not limited to specific embodiments and encompasses all modifications, equivalents or replacement s that fall within the spirit and technical scope of the present invention. In the following description, the detailed description of related known technology will be omitted when it may obscure the subject matter of the present invention.

Terms used in this specification are used only to describe a specific embodiment and are not intended to limit the scope of the present invention. Singular expressions are intended to include plural expressions unless specified otherwise in the context thereof. In this specification, the terms "comprise", "have", etc., are intended to denote the existence of mentioned characteristics, numbers, steps, operations, components, parts, or combinations thereof, but do not preclude the probability of existence or addition of one or more other characteristics, numbers, steps, operations, components, parts, or combinations thereof.

Unless otherwise defined, all technical and scientific terms used herein have the same meaning as commonly understood by those skilled in the art to which the present invention belongs.

A first aspect of the present invention is directed to a vector pair for screening tau oligomer formation, the vector pair comprising: a first vector comprising a first tau gene, a first fluorescence protein gene and a first neuron-specific promoter; and a second vector comprising a second tau gene, a second fluorescence protein gene and a second neuron-specific promoter, wherein a protein expressed from the first fluorescence protein gene and a protein expressed from the second fluorescence protein gene bind to each other to display fluorescence, by association between a protein expressed from the first tau gene and a protein expressed from the second tau gene.

The first tau gene and/or the second tau gene may be a full-length tau, a fragment of the full-length tau, or a variant of the full-length tau. For example, the tau gene may be human full-length tau gene Tau-P301L, but is not limited thereto. In an example of the present invention, a full-length tau gene represented by SEQ ID NO: 1 was used.

Tau protein is a kind of microtubule-associated protein (MAP) having a molecular weight of 50,000 to 70,000, and it is known that abnormal tau aggregation is a primary pathological hallmark in Alzheimer's disease (AD) and multiple other neurodegenerative disorders, collectively called tauopathies (Biochimica. et biophysica. acta. 1739: 331-354). In a healthy neuron, tau stabilizes microtubules by promoting axonal outgrowth and neuronal cell polarization. When pathologically hyperphosphorylated, tau dissociates from microtubules and forms insoluble aggregates (Mol. Neurodegener. 4: 13). A structural framework for tau aggregation has been suggested for many years. Evidences have been suggested that insoluble filaments are formed from 10 soluble monomers, and such filaments associate into higher order structures, called neurofibrillary tangles (NFTs). However, the pathophysiological importance of neurofibrillary tangles in tauopathies, the causes and molecular mechanisms responsible for triggering the process remain largely unknown, and this is because there is no reliable method for monitoring tau aggregation under physiological conditions. Until now, most studies on tau aggregation have been conducted using purified tau or tau fragments under non-physiological conditions. Furthermore, due to its extreme solubility, tau aggregation needs to be induced artificially by adding cofactors such as heparin. For this reason, animal models that can induce and monitor tau oligomer formation in living animals may provide a useful tool to investigate tau pathology and to discover methods capable of preventing and restoring the process.

The first fluorescence protein and/or the second fluorescence protein is one allowing proteins expressed from the first and second first fluorescence proteins to bind to each other to display fluorescence, by association between proteins expressed from the first tau gene and the second tau gene. Namely, when proteins expressed from the first tau gene and the second tau gene interact with each other, first fluorescence protein and the second fluorescence protein bind to each other simultaneously with or subsequently to the interaction to thereby display fluorescence. For example, the fluorescence protein may be a Venus protein. In addition, the first fluorescence protein gene may be represented by SEQ ID NO: 3, and the second fluorescence protein gene may be represented by SEQ ID NO: 5.

The present invention is an application of a method for visualizing protein-protein interactions that is based on a bimolecular fluorescence complementation (BiFC) technique of forming a fluorescence protein complex from non-fluorescent constituents attached to the proteins of interest (Annu. Rev. Biophys. 37: 465-487). Previously, a split green fluorescence protein (GFP) complementation technique was used to quantify tau aggregation. In the assay, tau is fused to a smaller GFP fragment (GFP 11), and co-expressed in cells with a larger GFP fragment (GFP 1-10). When tau exists as a monomer or low degree aggregate, the large GFP fragment is able to access the small GFP fragment fused to tau, leading to the association of the fluorescently active GFP. However, when tau aggregates, the reconstitution of active GFP is inhibited and GFP fluorescence decreases in cells. As a method of quantifying tau aggregation, the split-GFP assay has been highlighted; however, the limited scope and resolution of the assay do not allow the monitoring of tau oligomers that cause neuronal toxicity.

The BiFC technique based on the Venus protein, a kind of yellow fluorescence protein (YFP), is based on the principle according to which, when two different target proteins approach each other for interaction, fluorescence protein fragments linked to the target proteins also approach each other, and as a result, reconstitution between the fluorescence protein fragments occurs to display fluorescence. The use of this technique makes it possible to visually observe that an interaction between two target proteins occurred. Thus, this technique has the advantage of enabling protein-protein interactions to be visually observed in an optimal physical/chemical environment in which protein-protein interactions in cells or tissue may occur and be maintained. This technique makes it possible to determine not only a position where protein-protein interactions in cells or tissue occur, but also information about movement of these proteins.

The protein that is used in the present invention may be the Venus protein. The Venus protein can be effectively used for analysis of proteins such as tau protein, which are difficult to analyze spatially and temporally, because (1) it has fast and efficient maturation, (2) its self-assembly rate is low compared to that of other BiFC pairs, and (3) the fluorescence intensity of Venus-based BiFC is 10 times higher than that of EYFP-based BiFC (Biotechniques 40: 61-66; Biotechniques 49: 793-805).

According to one embodiment of the present invention, the first tau gene and the first fluorescence protein gene may be operably linked to each other, and the second tau gene and the second fluorescence protein gene may be operably linked to each other. Namely, in each of the first vector and the second vector, the tau gene and the fluorescence protein gene are preferably sequentially expressed by a single promoter. For example, the first tau gene and the first fluorescence protein gene may be linked to each other by a first linker, and the second tau gene and the second fluorescence protein gene may be linked to each other by a second linker. In an example of the present invention, the first linker represented by SEQ ID NO: 2 and the second linker represented by SEQ ID NO: 4 were used.

The first neuron-specific promoter and/or the second neuron-specific promoter serves to express the vector pair of the present invention, is not particularly limited, and may comprise any promoter known in the art. For example, the first neuron-specific promoter and/or the second neuron-specific promoter is preferably a Thy1 promoter. Since the Thy1 promoter is expressed specifically in neurons, it can induce expression of the genes inserted in the vector in neurons or neural tissue, particularly brain tissue.

The present invention is characterized in that, when a protein expressed from the first fluorescence protein gene and a protein expressed from the second fluorescence protein gene bind to each other to display fluorescence, by association between a protein expressed from the first tau gene and a protein expressed from the second tau gene. Particularly, the present invention is characterized in that the genes inserted in the vector can be expressed by the neuron-specific promoter in neurons or neural tissue, particularly brain tissue. Accordingly, tau oligomer formation in the mouse brain can be visualized directly by fluorescence, thereby monitoring and quantifying the tau oligomerization process in the brain.

According to one embodiment of the present invention, each of the first vector and the second vector, which comprise the Thy1 promoter, may be a pTSC21K vector comprising the Thy1 promoter, but is not limited thereto.

Furthermore, the first tau gene, the first fluorescence protein gene and the first linker may be inserted into the XhoI site of the pTSC21K vector, and the second tau gene, the second fluorescence protein gene and the second linker may be inserted into the XhoI site of the pTSC21K vector, but the scope of the present invention is not limited thereto.

Moreover, the first vector may comprise a nucleotide sequence of SEQ ID NO: 6, and the second vector may comprise a nucleotide sequence of SEQ ID NO: 7, but the scope of the present invention is not limited thereto.

In addition, the present invention may be directed to a vector pair for screening tau oligomer formation, comprising: a first vector which comprises a Thy1 promoter and wherein a full-length tau gene represented by SEQ ID NO: 1, a first linker represented by SEQ ID NO: 2, and a first fluorescence protein gene represented by SEQ ID NO: 3 are operably linked to one another; and a second vector which comprises a Thy1 promoter and wherein a full-length tau gene represented by SEQ ID NO: 1, a second linker represented by SEQ ID NO: 4, and a second fluorescence protein gene represented by SEQ ID NO: 5 are operably linked to one another.

A second aspect of the present invention is directed to a mouse embryo for screening tau oligomer formation, which has introduced therein the vector pair according to the first embodiment of the present invention.

The mouse and its embryo are not particularly limited. When this mouse embryo is used, a mouse can be obtained in which a protein expressed from the first fluorescence protein gene and a protein expressed from the second fluorescence protein gene bind to each other to display fluorescence, by association between a protein expressed from the first tau gene and a protein expressed from the second tau gene in neuronal tissue.

In according to one embodiment of the present invention, the mouse embryo may be a mouse embryo deposited in the Korean Collection for Type Cultures under accession number KCTC13076BP, but is no limited thereto. The date of the deposit is Aug. 16, 2016, and the address of the depository is Korea Research Institute of Bioscience and Biotechnology (KRIBB) 181, Ipsin-gil, Jeongeup-si, Jeollabuk-do 56212, Republic of Korea, The present inventors obtained a mouse embryo using the above-described vector pair, and produced a transgenic mouse from the mouse embryo, and confirmed the target gene in the transgenic mouse. In this process, a mouse embryo, showing high gene expression levels and enabling fluorescence to be easily observed, was selected and deposited.

A third aspect of the present invention is directed to a transgenic model mouse of neurological disease, which is obtained from the mouse embryo according to the second aspect of the present invention. For example, the neurological disease is preferably a neurodegenerative brain disease, particularly dementia.

In the transgenic model mouse, human full-length tau proteins and two kinds of Venus proteins (VN173 and VC155) linked thereto, respectively, are expressed by a Thy1 promoter. The Thy promoter operates specifically in neurons, and thus when the tau proteins having VN173 and VC155, respectively, form an oligomer in the brain of the mouse, BiFC fluorescence is displayed by the Venus proteins. According to this principle, whether or not a tau oligomer would be formed in the brain tissue of the mouse and the extent of tau oligomer formation can be visually observed.

According to one embodiment of the present invention, the transgenic mouse may be a mouse wherein fluorescence is displayed by binding between the first fluorescence protein and the second fluorescence protein, when the full-length tau expressed from the first vector and the full-length tau expressed from the second vector form an oligomer. However, the transgenic mouse of the present invention is not limited thereto.

A fourth aspect of the present invention is directed to a method of detecting tau oligomer formation using a transgenic model mouse, the method comprising the steps of: obtaining a brain tissue section from the brain of the transgenic model mouse according to the third aspect of the present invention; subjecting the obtained brain tissue section to imaging analysis to measure fluorescence intensity; and comparing the measured fluorescence intensity with a reference value.

The step of obtaining the brain tissue section may comprises injecting a tau aggregation inducer into the transgenic model mouse and obtaining the brain tissue section from the brain of the transgenic model mouse injected with the tau aggregation inducer.

A fifth aspect of the present invention is directed to a method for screening a tau oligomer formation inhibitor candidate, the method comprising the steps of: inducing tau oligomer formation in the brain of the transgenic model mouse; evaluating the level of tau oligomer formation in the brain of the transgenic model mouse; administering a tau oligomer formation inhibitor candidate to the transgenic model mouse; evaluating the level of tau oligomer formation in the brain of the transgenic model mouse; and comparing the level of tau oligomer formation between before and after administering the tau oligomer formation inhibitor candidate.

For example, the step of evaluating the level of tau oligomer formation may comprise quantifying the fluorescence intensity of the fluorescence protein, that is, the Venus protein, but is not limited thereto.

According to one embodiment of the present invention, the step of inducing tau oligomer formation in the brain of the transgenic model mouse may comprise administering forskolin or okadaic acid to the transgenic model mouse, but is not limited thereto. The forskolin or the okadaic acid may be used to induce hyperphosphorylation of tau protein.

BRIEF DESCRIPTION OF THE DRAWINGS

FIGS. 2A and 2B are schematic views showing the results of sequencing of pTSC21K-TauP301L-VN173 and pTSC21K-TauP301L-VC155 recombinant plasmids, respectively, used in an example of the present invention.

DETAILED DESCRIPTION OF THE INVENTION

Figure 1A:
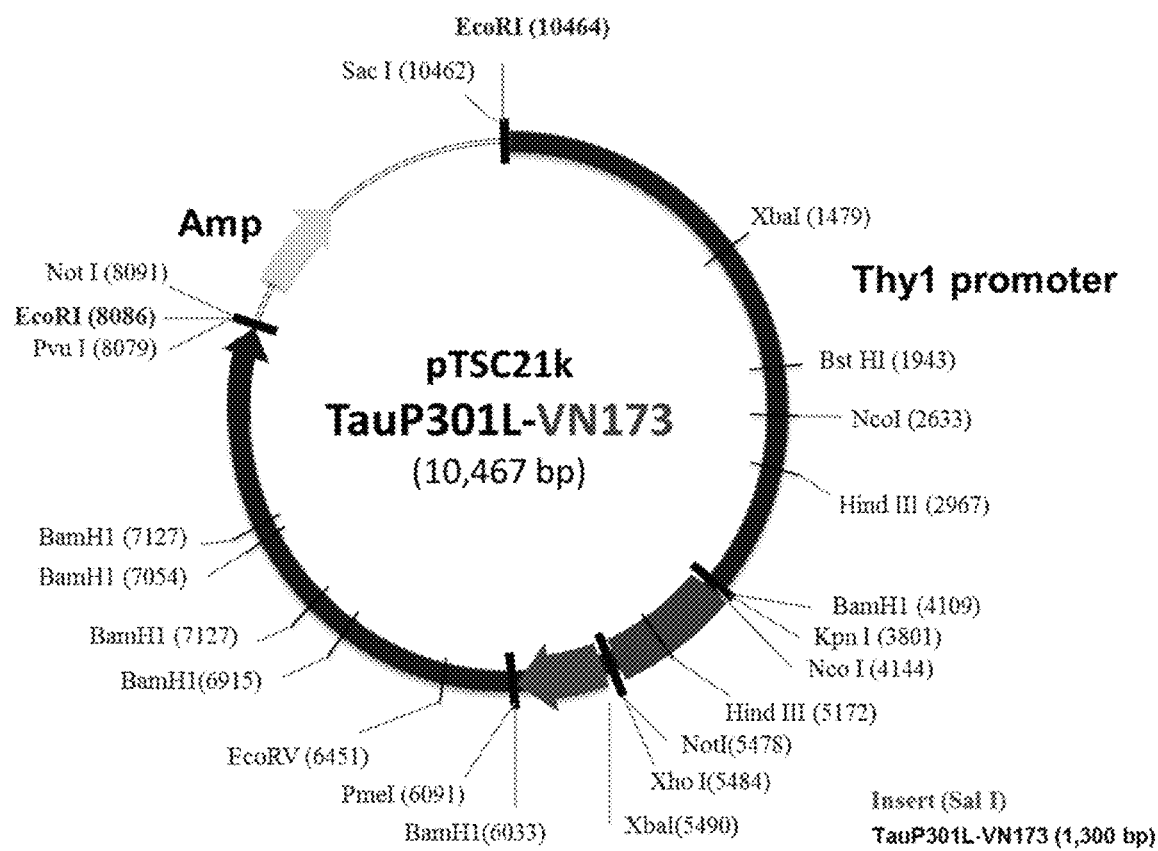
FIGS. 1A and 1B are schematic views showing the structures of pTSC21K-TauP301L-VN173 and pTSC21K-TauP301L-VC155 recombinant plasmids, respectively, used in an example of the present invention.

Hereinafter, the present invention will be described in further detail with reference to examples. It is to be understood, however, that these examples are for illustrative purposes only and are not intended to limit the scope of the present invention as defined in the appended claims.

EXAMPLES

1. Construction of Neuron-Specific Vectors for Screening Tau Oligomer Formation

To express tau protein specifically in mouse neurons, two bimolecular fluorescence complementation (BiFC) constructs (tau-VN173 and tau-VC155) were cloned into 323-pTSC21K vectors including a Thy1 promoter.

Particularly, in the present invention, vectors were constructed using a Venus-based BiFC system. To this end, the mammalian expression vector pCMV6-hTau40-GFP was purchased from OriGene Technologies Inc. (Rockville, Md., USA), and the amino acid proline at position 301 was replaced with leucine, thereby constructing pCMV6-hTau40P301 L-GFP. The forward and reverse primer sequences used herein are shown in Table 1 below.

TABLE 1

| P301L-F | 5'-AAT ATC AAA CAC GTC CTG GGA GGC GGC AGT G-3' (SEQ ID NO: 8) |
|---|---|
| P301L-R | 5'-CAC ACT GCC GCC TCC CAG GAC GTG TTT-3' (SEQ ID NO: 9) |

To replace GFP with a Venus fluorescence protein fragment, pBiFC-VN173 and pBiFC-VC155 were purchased from Addgene (Cambridge, Mass.), and then amplified using PCR primers having XhoI/PmeI restriction enzyme sequences. Next, a substituted human full-length tau (441 amino acids) was fused to the N-terminal fragment (1-172, VN173) (first fluorescence protein) and C-terminal fragment (155-238, VC155) (second fluorescence protein) of the fluorescence protein Venus.

pCMV6-TauP301L-GFP and the PCR-amplified insert were digested with XhoI/PmeI and ligated with each other, thereby constructing pCMV6-TauP301L-VN173 and pCMV6-TauP301L-VC155 which are insertion genes. The linker peptide and fluorescence protein sequences used in construction of the insertion genes are shown in Tables 2 and 3 below.

TABLE 2

| pCMV6-TauP301L-VN173 | |
|---|---|
| First linker peptide | ACGCGTACGCGGCCGCTCGAGTCTAGAAGATCC ATCGCCACC (SEQ ID NO: 2) |
| First fluorescence protein (VN173) | ATGGTGAGCAAGGGCGAGGAGCTGTTCACCGGG GTGGTGCCCATCCTGGTCGAGCTGGACGGCGAC GTAAACGGCCACAAGTTCAGCGTGTCCGGCGAG GGCGAGGGCGATGCCACCTACGGCAAGCTGACC CTGAAGCTGATCTGCACCACCGGCAAGCTGCCC GTGCCCTGGCCCACCCTCGTGACCACCCTGGGC TACGGCCTGCAGTGCTTCGCCCGCTACCCCGAC CACATGAAGCAGCACGACTTCTTCAAGTCCGCC ATGCCCGAAGGCTACGTCCAGGAGCGCACCATC TTCTTCAAGGACGACGGCAACTACAAGACCCGC GCCGAGGTGAAGTTCGAGGGCGACACCCTGGTG AACCGCATCGAGCTGAAGGGCATCGACTTCAAG GAGGACGGCAACATCCTGGGGCACAAGCTGGAG TACAACTACAACAGCCACAACGTCTATATCACC GCCGACAAGCAGAAGAACGGCATCAAGGCCAAC TTCAAGATCCGCCACAACATCGAGTAG (SEQ ID NO: 3) |

TABLE 3

| pCMV6-TauP301L-VC155 | |
|---|---|
| Second linker peptide | ACGCGTACGCGGCCGCTCGAGAAG (SEQ ID NO: 4) |
| Second fluorescence protein (VC155) | CAGAAGAACGGCATCAAGGCCAACTTCAAGATC CGCCACAACATCGAGGACGGCGGCGTGCAGCTC GCCGACCACTACCAGCAGAACACCCCCATCGGC GACGGCCCCGTGCTGCTGCCCGACAACCACTAC CTGAGCTACCAGTCCAAACTGAGCAAAGACCCC AACGAGAAGCGCGATCACATGGTCCTGCTGGAG TTCGTGACCGCCGCCGGGATCACTCTCGGCATG GACGAGCTGTACAAGTAA (SEQ ID NO: 5) |

The Thy1 promoter from mouse thy1.2 gene is a promoter that is expressed specifically in mouse brain neurons. Mouse Thy1 gene (mouse Thy-1.2 glycoprotein gene) is 5572 bp in total length and includes three exon regions and three intron regions. TauP301L-VN173 and Tau-P301L-VC155 were inserted into exon 3 of the Thy1 gene.

Figure 1B:
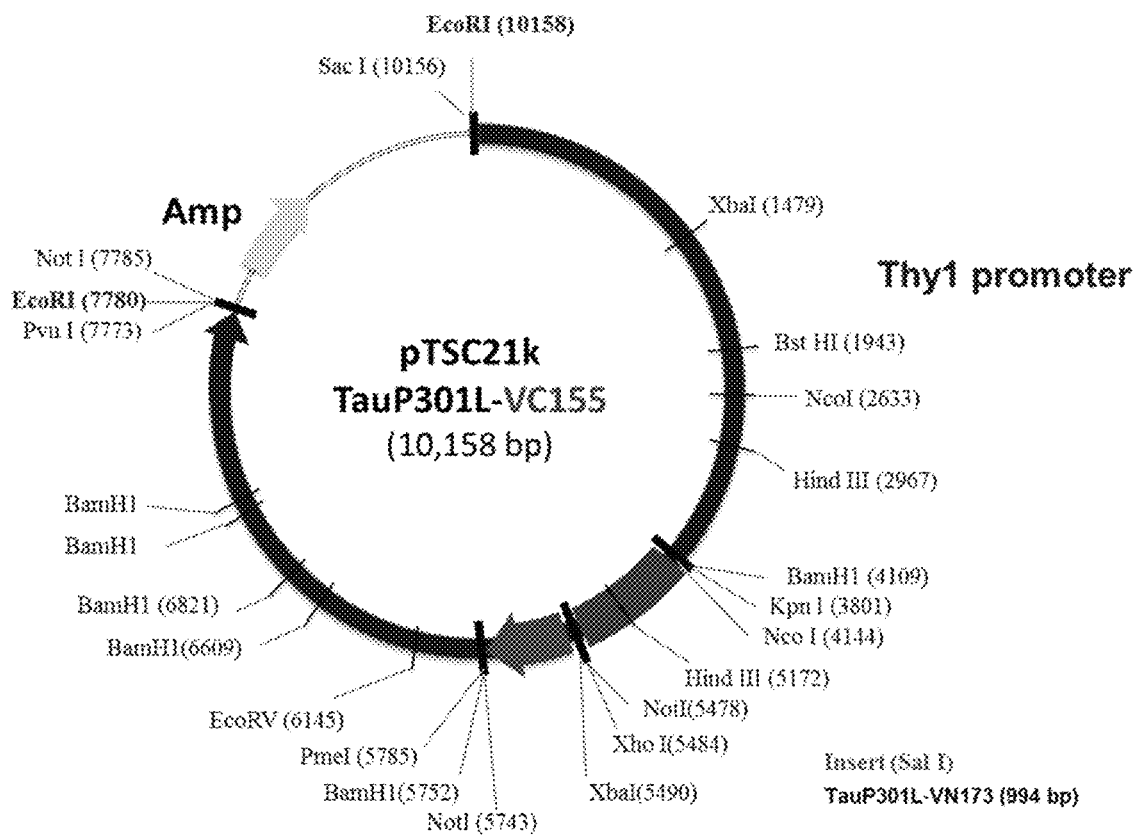
Figure 2A:
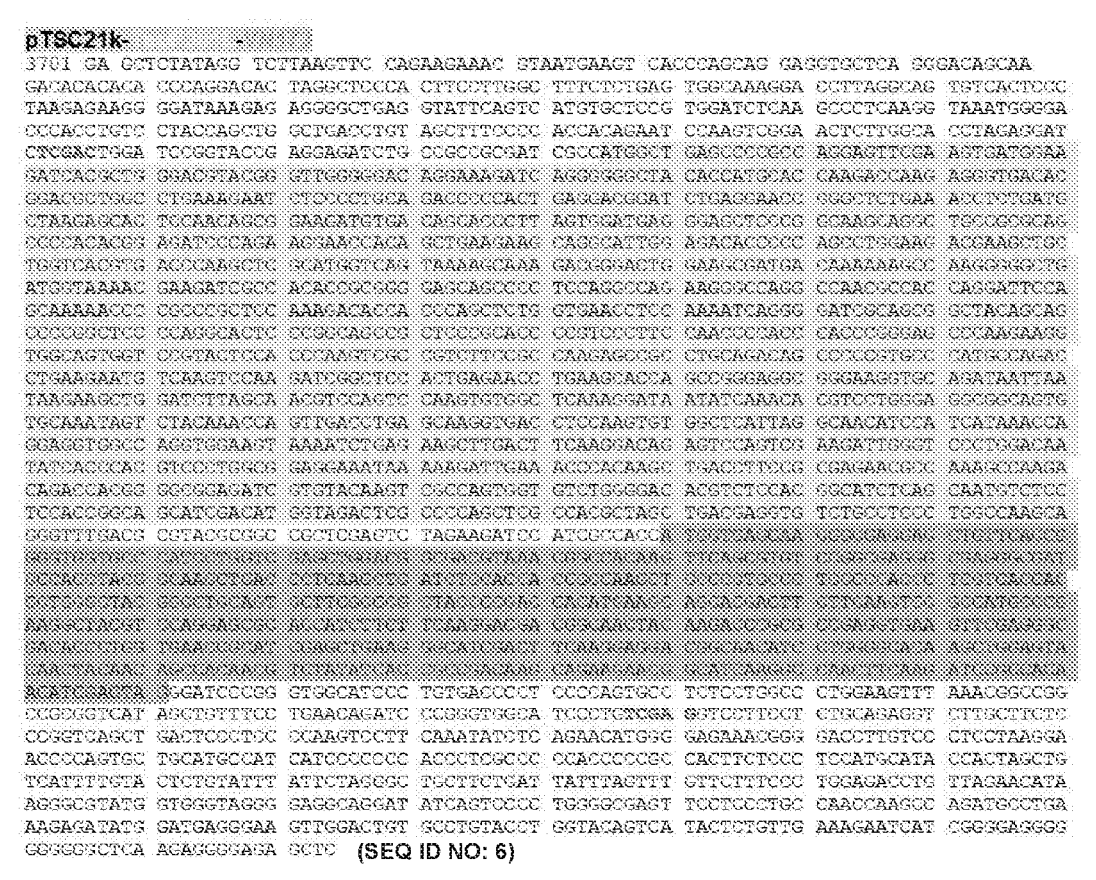
Figure 2B:
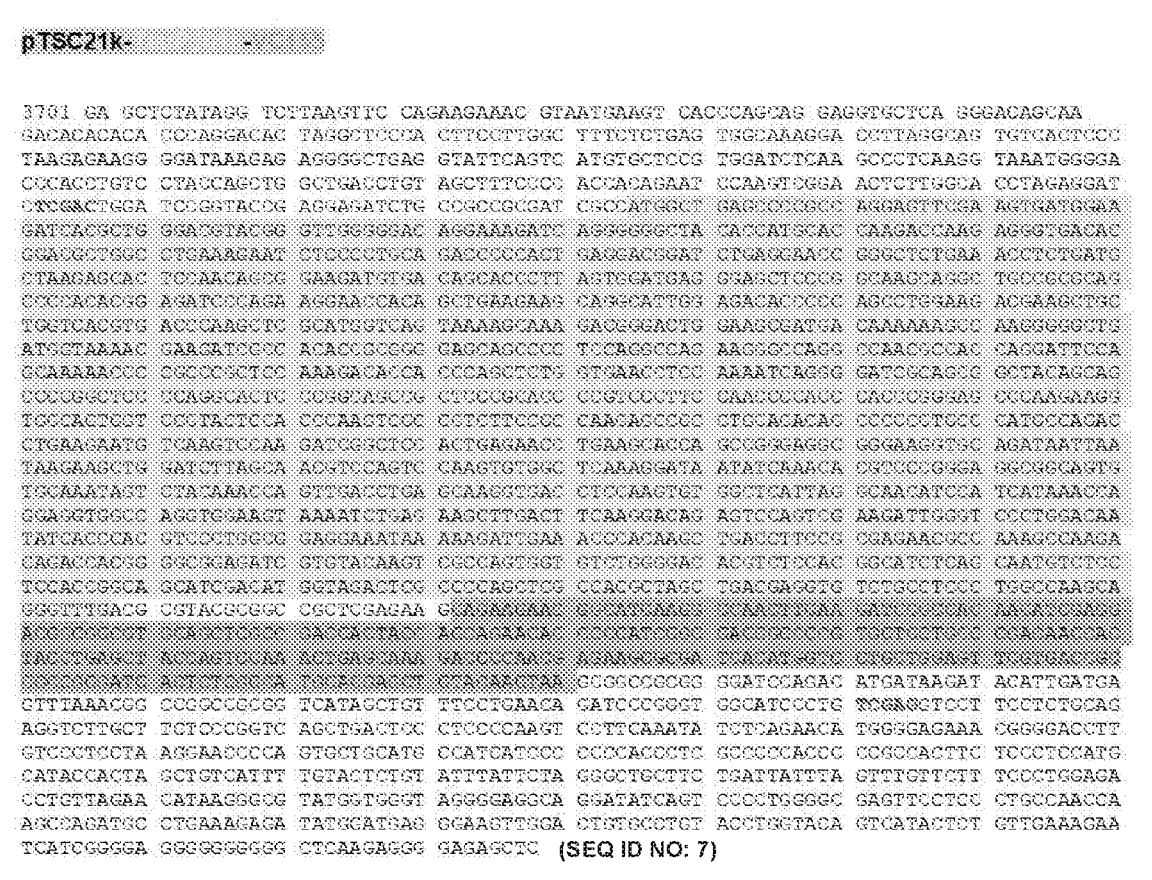
Figure 3:
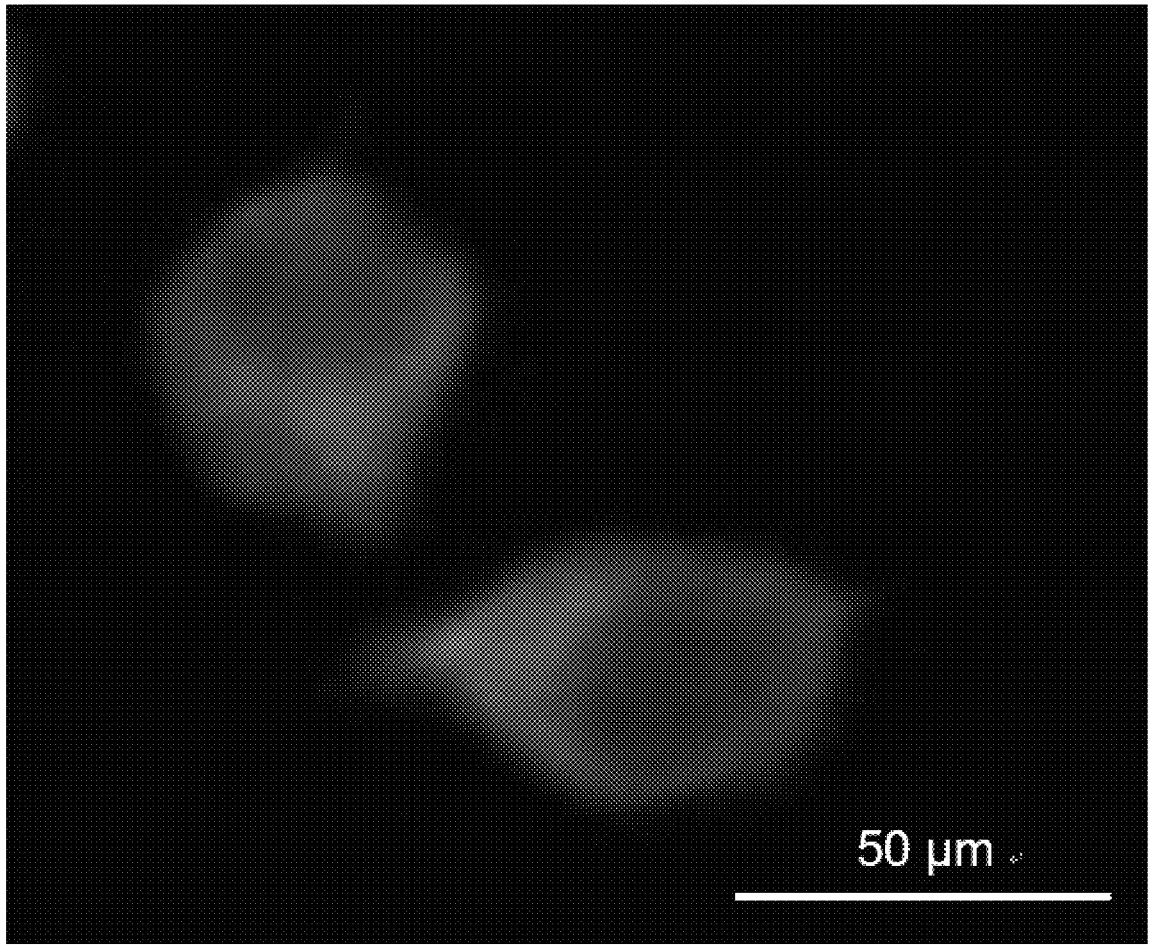
FIG. 3 is an image showing the results of analyzing BiFC fluorescence displayed by tau oligomer formation in SH-SY5Y cells introduced with pTSC21K-TauP301L-VN173 and pTSC21K-TauP301L-VC155 recombinant plasmids in an example of the present invention.

Each of two tau-BiFC plasmids (i.e., pCMV6-TauP301L-VN173 and pCMV6-TauP301L-VC155) prepared as insertion genes was cloned into the Xho-1 site of a 323-pTSC21K vector. FIGS. 1A and 1B show the above-constructed pTSC21K-TauP301L-VN173 and pTSC21K-TauP301L-VC155 recombinant plasmids, respectively. After the re-cloning process, in order to confirm whether pTSC21K-TauP301L-VN173 and pTSC21KTauP301L-VC155 would be successfully constructed, the insert region and surrounding region of the two recombinant plasmids were sequenced. FIGS. 2A and 2B show the sequences of the recombinant plasmids. Then, in order to examine expression of TauP301L-BiFC under the control of the Thy1 promoter, the recombinant plasmids were transduced into SH-SY5Y cells, and 24 hours, normal expression of TauP301L-BiFC in the neuronal cells was observed. FIG. 3 shows a fluorescence microscopic image of the SH-SY5Y cells expressing TauP301L-BiFC.

2. Construction of Transgenic Model Mice

Figure 4:
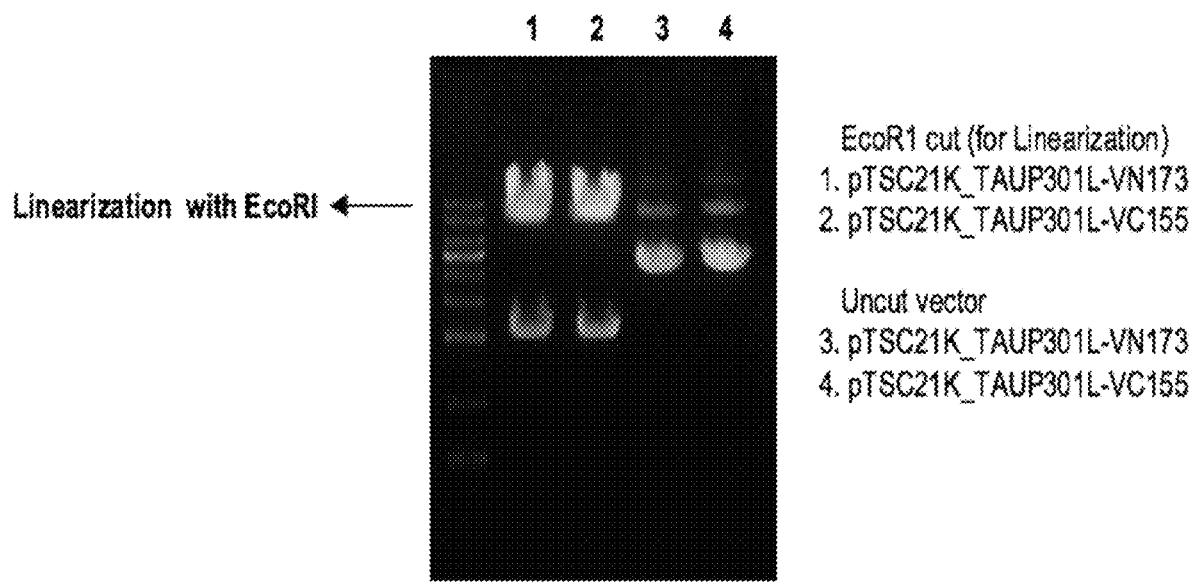
FIG. 4 is an image showing the results of electrophoresis performed after linearization of each of pTSC21K-TauP301L-VN173 and pTSC21K-TauP301L-VC155 recombinant plasmids constricted in an example of the present invention.
Figure 5:
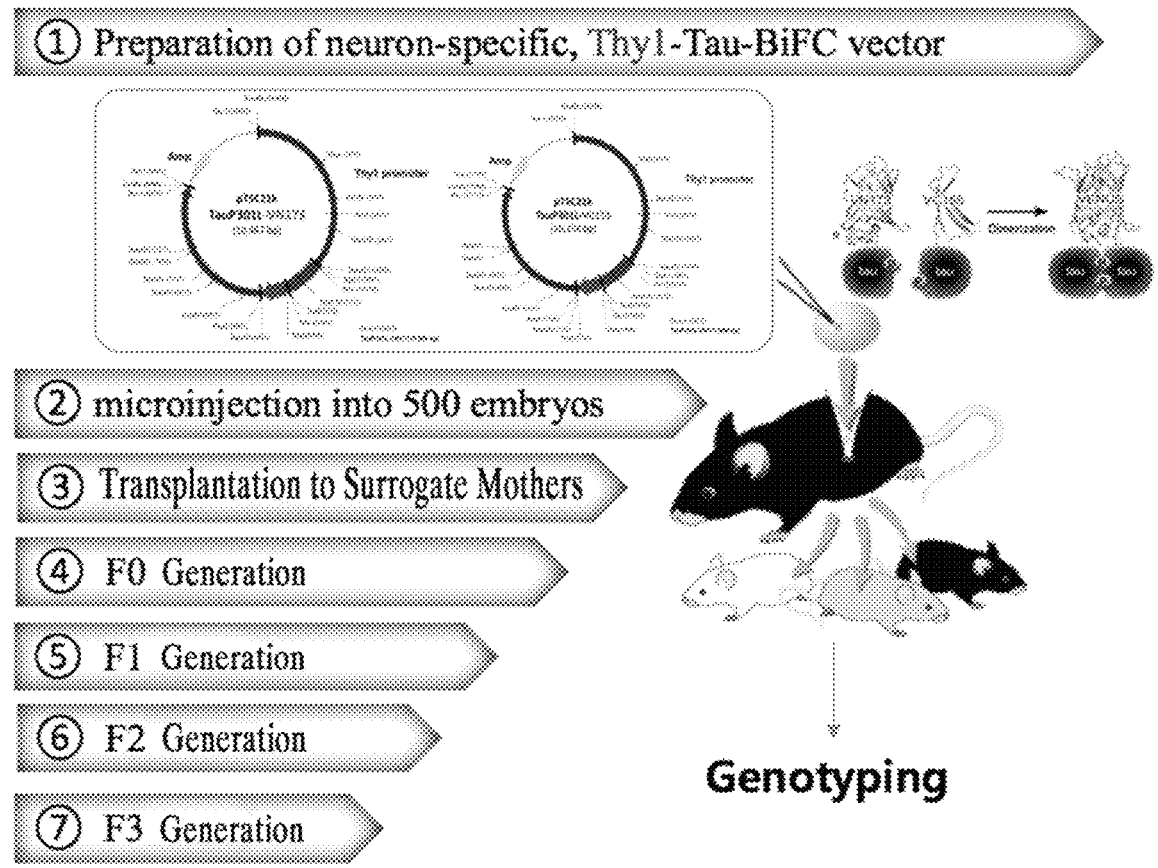
FIG. 5 is a schematic view showing a method for constructing a transgenic mouse according to an embodiment of the present invention.
Figure 6:
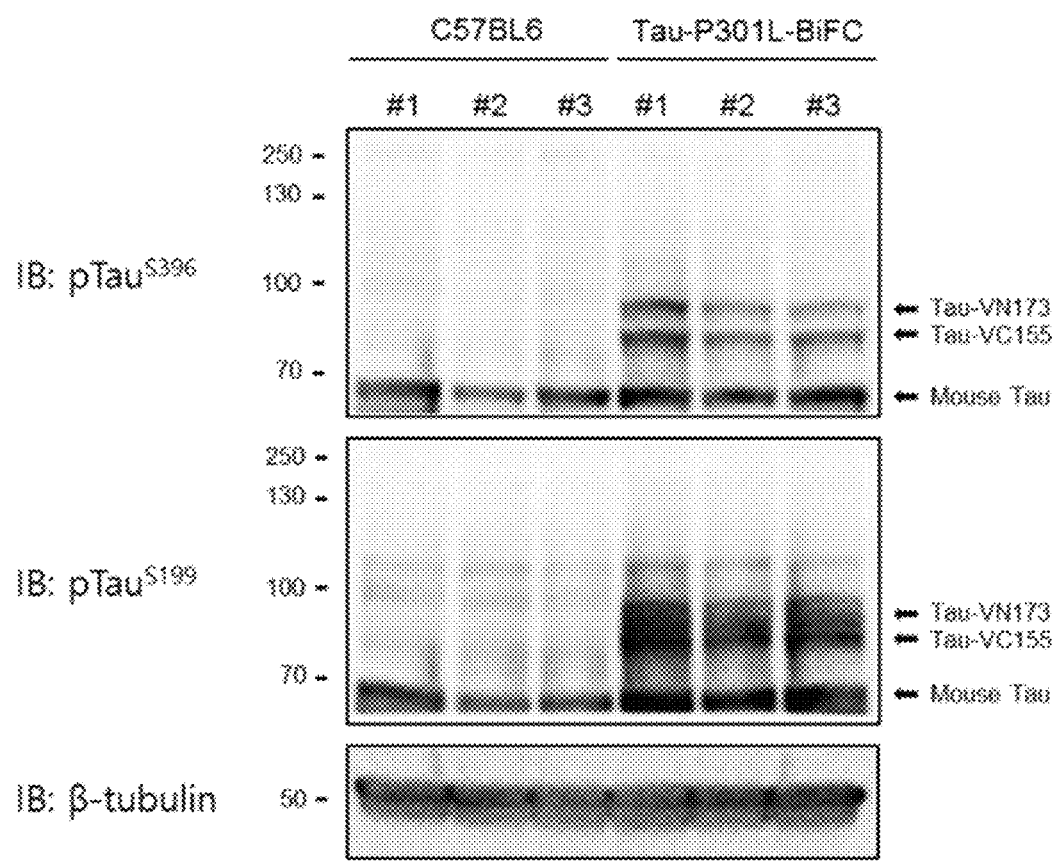
FIG. 6 shows the results of Western blot analysis performed to determine whether or not TauP301L-VN173 and TauP301L-VC155 proteins in transgenic mice constructed in an example of the present invention would be normally expressed.

For injection into mouse embryos, the Thy1-TauP301L-VN173 and Thy1-Tau-P301L-VC155 recombinant plasmids were linearized with the restriction enzyme EcoRI. FIG. 4 shows the results of electrophoresis of the plasmids linearized with EcoRI. To construct transgenic mice, the confirmed plasmids were injected into embryos. To obtain embryos, pregnant mare serum gonadotropin and human chorionic gonadotropin were injected into C57BL/6N female mice to induce superovulation. The superovulation-induced C57BL/6N female mice were mated with C57BL/6N male mice, and after mating, embryos were obtained from pregnant C57BL/6N female mice. Then, the vectors expressing Thy1-TauP301L-VN173 and Thy1-Tau-P301L-VC155 were injected into the male pronucleus of zygote of the obtained embryos, and the injected embryos were transferred into ICR surrogate mothers. Next, genotyping was performed to select mice having both TauP301L-VN173 and TauP301L-VC155 (FIG. 5). Next, in order to examine whether both the TauP301L-VN173 and TauP301L-VC155 proteins would be normally expressed by introduction of the genes, Western blotting analysis was performed. First, 3-month-old genetically modified mice were anesthetized, and the brain was extracted from each of the mice. The extracted brain was lysed in RIPA containing phosphatase and protease to prepare a brain lysate sample. 40 μg of the sample was loaded, and antigen-antibody reactions with tau antibodies (pS199 and pS396) targeting phosphorylated tau were analyzed. As a result, it was shown that TauP301L-VN173 and TauP301L-VC155 in the mice obtained from the mouse embryos injected with the vectors were normally expressed, unlike those in normal control mice (FIG. 6).

3. Observation of Tauopathy in Transgenic Mice

Figure 7:
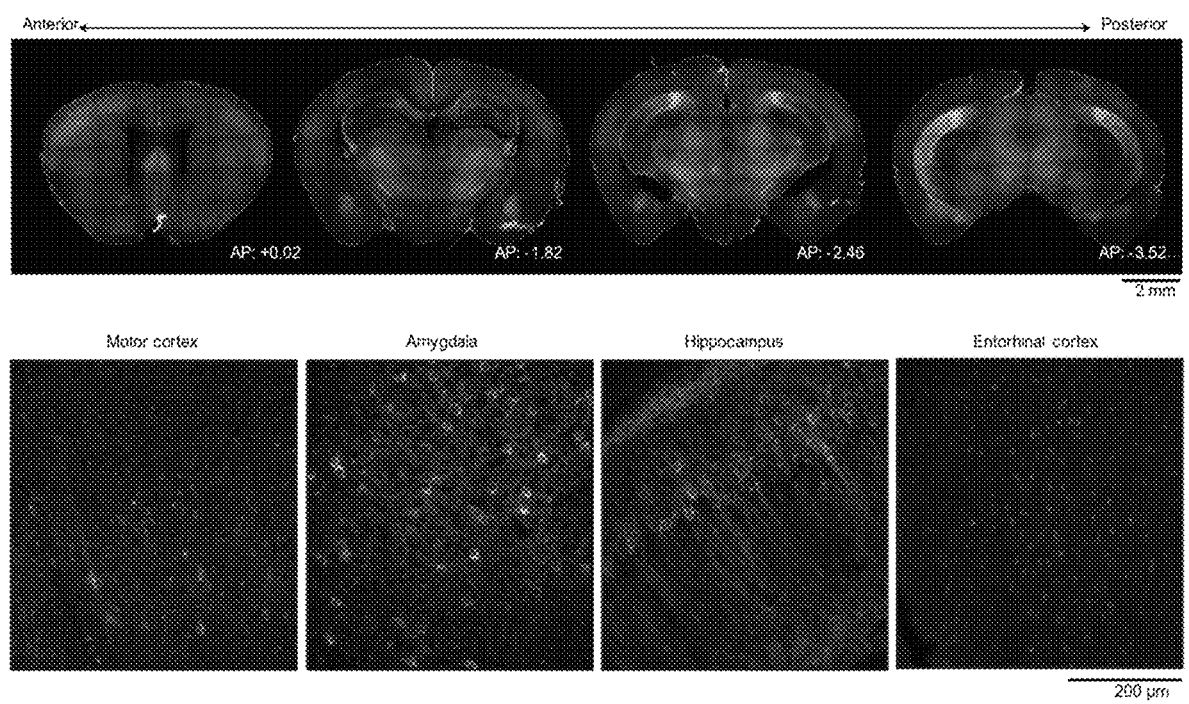
FIG. 7 depicts images showing BiFC fluorescence resulting from tau oligomer formation in the brain tissue of transgenic mice constructed in an example of the present invention.
Figure 8:
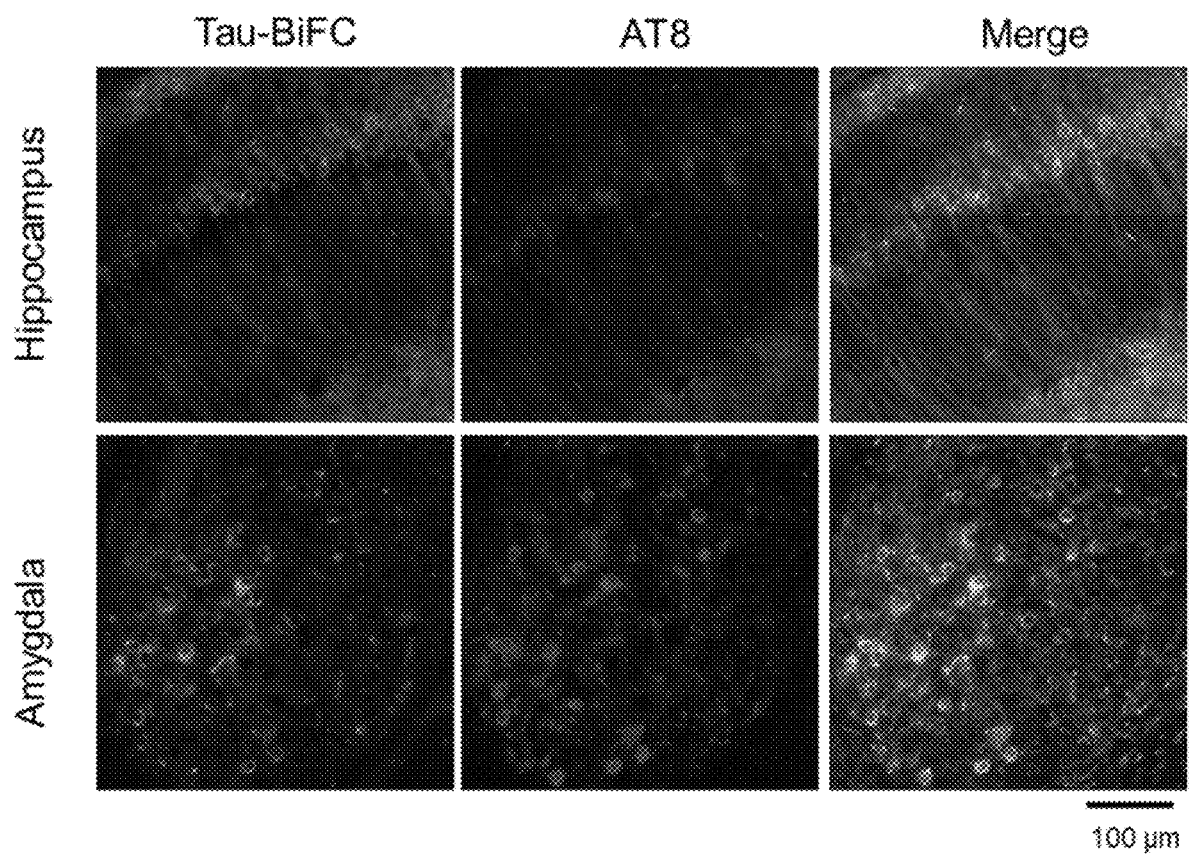
FIG. 8 depicts staining images comparing AT8 immunofluorescence with BiFC fluorescence resulting from tau oligomer formation in the brain tissue of transgenic mice constructed according to an example of the present invention.

The constructed Tau-P301L BiFC transgenic mice display fluorescence when tau protein formed oligomers in the brain. In order to actually confirm whether fluorescence would be observed by tau oligomer formation in the brain tissue of the Tau-P301L BiFC transgenic mice, the brain of 7-month-old mice was purfused, fixed, and extracted, and the extracted brain was sectioned to a thickness of 40 μm. The brain tissue sections of various regions were imaged without immunofluorescence staining, and as a result, BiFC fluorescence was observed. Specifically, BiFC fluorescence could be observed in the hippocampus, cortex, amygdale and the like of tau-expressing animal models known to show tau aggregation. FIG. 7 shows an image of BiFC fluorescence displayed in the brain tissue section. In order to verify that BiFC fluorescence displayed in the mouse brain tissue results from tau oligomer formation, immunofluorescence staining of the same brain tissue section with the tau antibody AT8 targeting phosphorylated tau was performed. As a result, it was shown that the BiFC fluorescence displayed was consistent with fluorescence labeled with AT8 (FIG. 8).

4. Observation of Induction of Tau Oligomer Formation in Transgenic Mice

Figure 9:
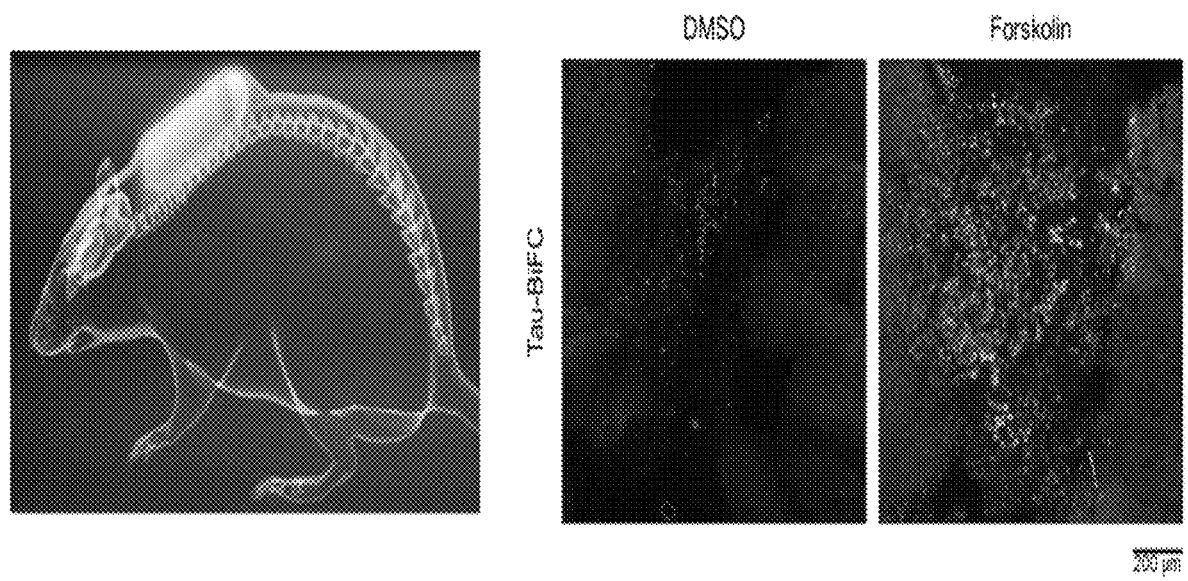
FIG. 9 depicts images showing the results of observing BiFC fluorescence in the brain tissue of a transgenic mouse injected with a tau oligomer formation inducer in an example of the present invention.

Using 4-month-old Tau-P301L BiFC transgenic mice which have not yet shown tau aggregation, whether tau oligomer BiFC fluorescence would be observed following injection of a tau aggregation inducer was examined. The tau aggregation inducing drug forskolin was filled in a drug injection kit, and then the drug was allowed to flow into a ventricle in the brain of about 5-month-old Tau-P301L BiFC transgenic mice (FIG. 9). After about 10 days of drug injection, brain section samples were made for observation of BiFC fluorescence. As a result, in the brain of the Tau-P301L BiFC transgenic mice injected with forskolin, BiFC fluorescence was observed in a portion surrounding the injected region, unlike mice injected with DMSO as a control. This result suggests that tau oligomer formation in the mouse brain was accelerated by injection of the forskolin drug. In addition, it was demonstrated that the level of tau oligomer formation could be directly observed without using a separate antibody.

As described above, according to the present invention, tau oligomer formation occurring in the brain of mice can be visualized directly by fluorescence, thereby monitoring and quantifying the tau oligomerization process in the brain. The use of this technology makes it possible to investigate diseases such as dementia in which tau protein is involved, and to screen a tau oligomer formation inhibitor candidate. Thus, the present invention may be used as a useful tool in development of dementia therapeutic agents.

While the present invention has been described with reference to the particular illustrative embodiments, it will be understood by those skilled in the art to which the present invention pertains that the present invention may be embodied in other specific forms without departing from the technical spirit or essential characteristics of the present invention. Therefore, the embodiments described above should be considered in a descriptive sense only and not for purposes of limitation. For example, each component described in a single form may be carried out in a distributed fashion, and likewise, components described in a distributed form may be carried out in a combined fashion.

Therefore, the scope of the present invention is defined not by the detailed description, but by the claims and their equivalents, and all variations within the scope of the claims and their equivalents are to be construed as being included in the scope of the present invention.

What is claimed is:

1. A transgenic mouse whose genome comprises: a first expression vector comprising a first tau gene, a first fluorescence protein gene under the control of a first neuron-specific Thy-1 promoter; and a second expression vector comprising a second tau gene, a second fluorescence protein gene under the control of a second neuron-specific Thy-1 promoter,
wherein a protein expressed from the first fluorescence protein gene and a protein expressed from the second fluorescence protein gene bind to each other to display fluorescence, by association between a protein expressed from the first tau gene and a protein expressed from the second tau gene,
wherein the first tau gene and the first fluorescence protein gene are operably linked to each other, and the second tau gene and the second fluorescence protein gene are operably linked to each other, wherein the first expression vector and the second expression vector comprise the nucleotide sequence as set forth in SEQ ID NO: 6 and 7 respectively,
wherein the mouse exhibits fluorescence that is displayed by binding between the first fluorescence protein and the second fluorescence protein upon a full-length tau expressed from the first vector and a full-length tau expressed from the second vector forming an oligomer the hippocampus, cortex and amygdale.

2. A mouse embryo comprising a vector pair, comprising: a first expression vector comprising a first tau gene, a first fluorescence protein gene under control of a first neuron-specific thy-1 promoter; and a second expression vector comprising a second tau gene, a second fluorescence protein gene under control of a second neuron-specific thy-1 promoter, wherein a protein expressed from the first fluorescence protein gene and a protein expressed from the second fluorescence protein gene bind to each other to display fluorescence, by association between a protein expressed from the first tau gene and a protein expressed from the second tau gene, wherein the first tau gene and the first fluorescence protein gene are operably linked to each other, and the second tau gene and the second fluorescence protein gene are operably linked to each other, wherein the first expression vector and the second expression vector comprise the nucleotide sequence as set forth in SEQ ID NO: 6 and 7 respectively; and wherein said mouse embryo is capable of producing transgenic mouse of claim 1.

* * * * *